(12) United States Patent
Watakabe et al.

(10) Patent No.: US 9,938,494 B2
(45) Date of Patent: Apr. 10, 2018

(54) CELL DETACHMENT DEVICE

(71) Applicant: KAWASAKI JUKOGYO KABUSHIKI KAISHA, Kobe-shi, Hyogo (JP)

(72) Inventors: Keizo Watakabe, Kobe (JP); Junji Iizaka, Akashi (JP); Hitoshi Hasunuma, Kobe (JP); Katsumi Nakashima, Kobe (JP)

(73) Assignee: KAWASAKI JUKOGYO KABUSHIKI KAISHA, Kobe-shi (JP)

( * ) Notice: Subject to any disclaimer, the term of this patent is extended or adjusted under 35 U.S.C. 154(b) by 226 days.

(21) Appl. No.: 14/650,053

(22) PCT Filed: Dec. 6, 2013

(86) PCT No.: PCT/JP2013/007191
§ 371 (c)(1),
(2) Date: Jun. 5, 2015

(87) PCT Pub. No.: WO2014/091731
PCT Pub. Date: Jun. 19, 2014

(65) Prior Publication Data
US 2015/0315537 A1 Nov. 5, 2015

(30) Foreign Application Priority Data

Dec. 12, 2012 (JP) ................................. 2012-271566

(51) Int. Cl.
*C12M 3/00* (2006.01)
*C12M 1/00* (2006.01)
*C12M 1/26* (2006.01)

(52) U.S. Cl.
CPC .................................. *C12M 33/08* (2013.01)

(58) Field of Classification Search
CPC ...... C12M 23/04; C12M 23/10; C12M 23/12; C12M 23/48; C12M 35/04
See application file for complete search history.

(56) References Cited

U.S. PATENT DOCUMENTS 3,926,733 A    12/1975  Chibata et al.
4,208,484 A *  6/1980   Sogi ...................... B04B 5/0421
                                                    422/72

(Continued)

FOREIGN PATENT DOCUMENTS

DE    2 348 692 A1    4/1974
JP    S56-154988 A    11/1981

(Continued)

OTHER PUBLICATIONS

Feb. 4, 2014 Interntational Search Report issued in International Patent Application No. PCT/JP2013/007191.

(Continued)

*Primary Examiner* — Nathan A Bowers
(74) *Attorney, Agent, or Firm* — Oliff PLC

(57) ABSTRACT

A cell detachment device includes: a base; a vessel holder, to which a culture vessel is to be fitted; a guide mechanism configured to guide reciprocating movement of the vessel holder; a collided member configured to collide with the vessel holder when the vessel holder is moving; an urging member configured to urge the culture vessel toward the collided member; and a power imparting mechanism configured to impart, to the vessel holder, power for causing the vessel holder to move.

11 Claims, 4 Drawing Sheets

(56) References Cited

U.S. PATENT DOCUMENTS

| | | | |
|---|---|---|---|
| 4,224,281 A * | 9/1980 | Thieme | B01L 3/0206 222/52 |
| 4,556,639 A | 12/1985 | Izawa et al. | |
| 7,645,065 B2 | 1/2010 | Bae | |
| 7,892,490 B2 * | 2/2011 | Oh | B01L 3/502715 251/318 |
| 8,465,971 B2 * | 6/2013 | Kishida | C12M 35/04 435/288.1 |
| 2002/0044495 A1 | 4/2002 | Friedman | |
| 2004/0179866 A1 * | 9/2004 | Muramatsu | G03G 15/0874 399/258 |

FOREIGN PATENT DOCUMENTS

| | | |
|---|---|---|
| JP | S58-155087 A | 9/1983 |
| JP | S58-158182 A | 9/1983 |
| JP | H08-85483 A | 4/1996 |
| JP | H10-229684 A | 8/1998 |
| JP | 2008-079554 A | 4/2008 |
| JP | 2010-142143 A | 7/2010 |
| JP | 2011-174294 A | 9/2011 |

OTHER PUBLICATIONS

Jul. 22, 2016 Extended Search Report issued in European Patent Application No. 13863213.8.

\* cited by examiner

[FIG.1]
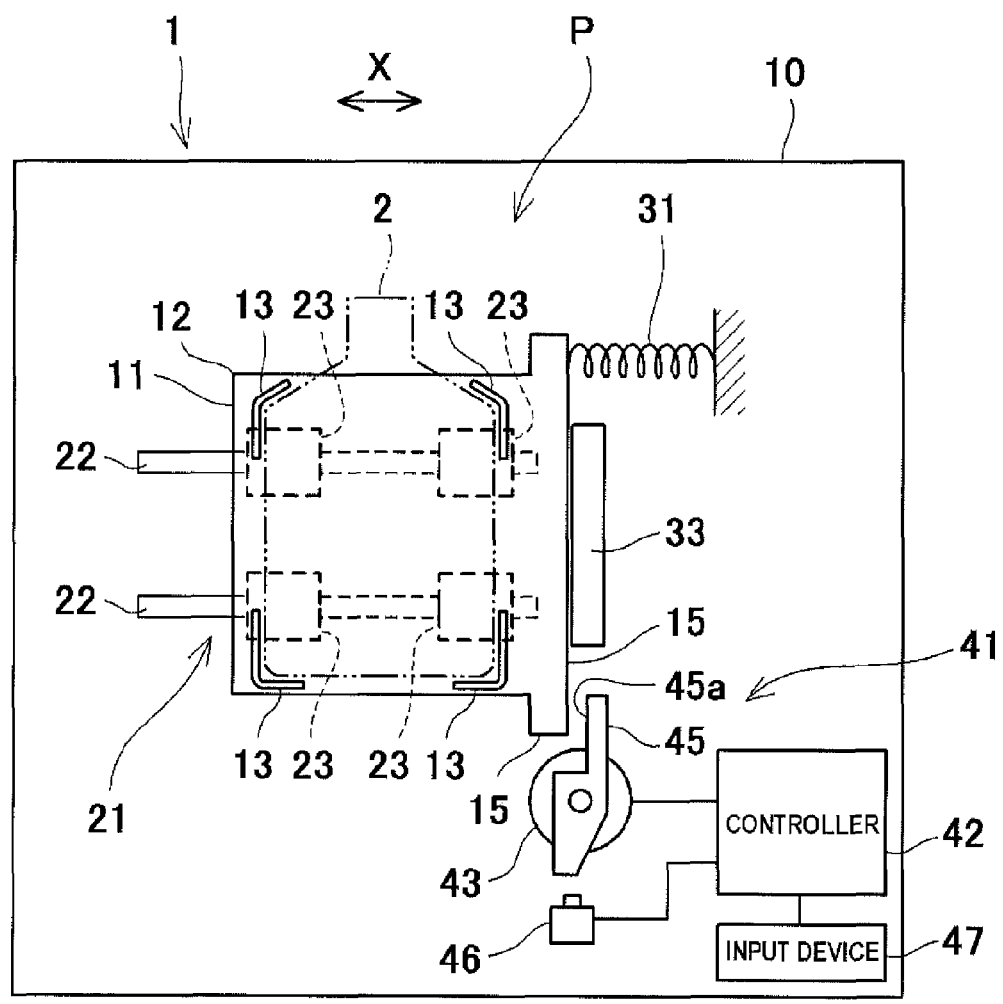

[FIG.2]
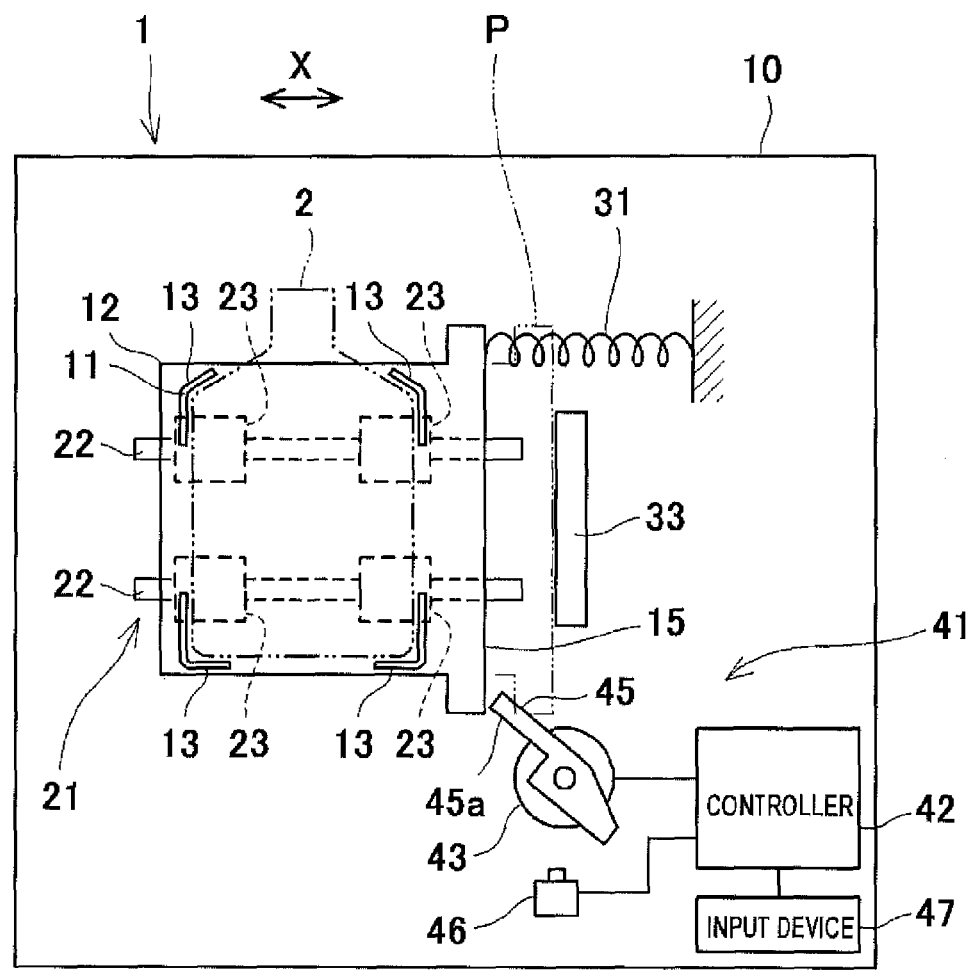

[FIG.3]
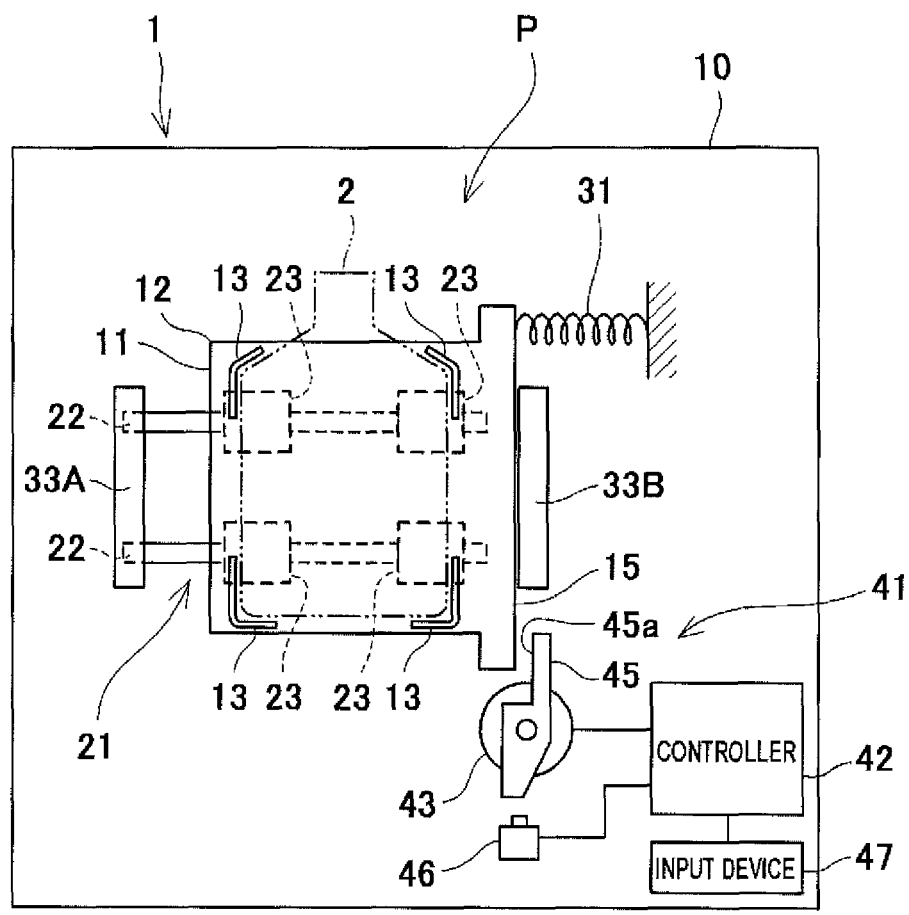

[FIG.4]
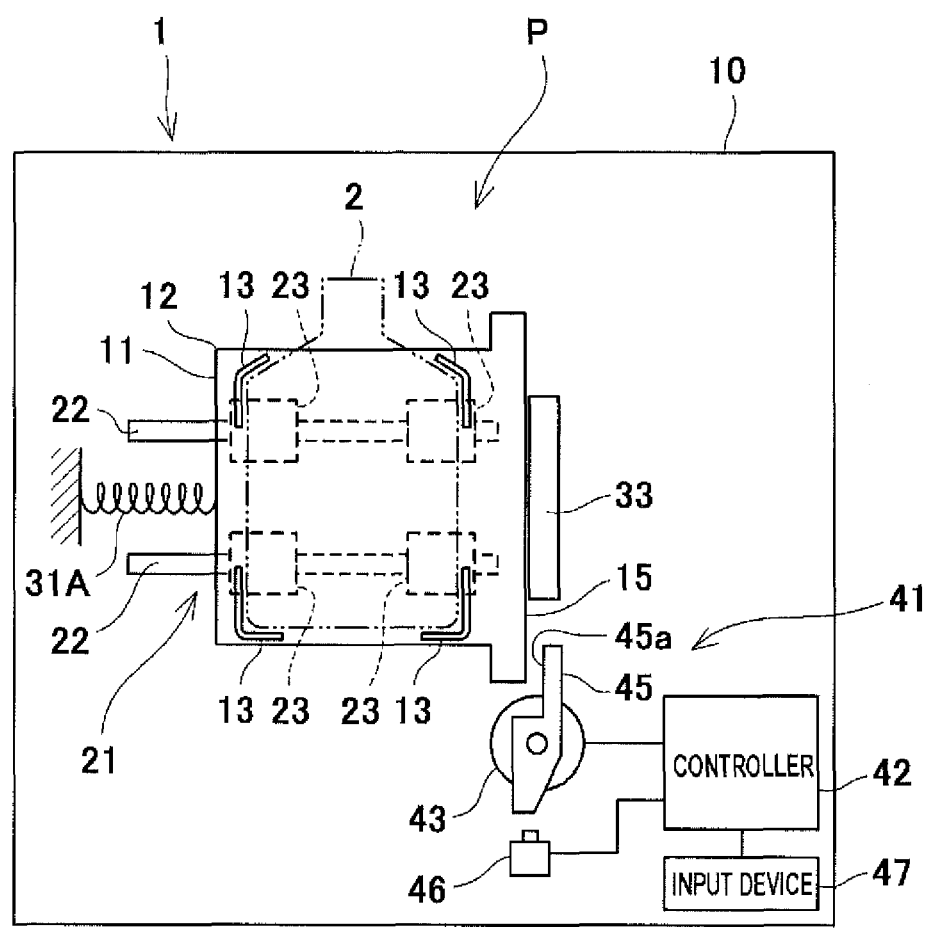

CELL DETACHMENT DEVICE

TECHNICAL FIELD

The present invention relates to a device for use in cell culturing and particularly to a device for detaching cultured cells growing on the culture surface of a culture vessel from the culture surface.

BACKGROUND ART

In recent years, cell culturing techniques for culturing cells and regenerative medical techniques utilizing cultured cells have been drawing attention. One of the important operations in cell culturing is cell subculturing. Generally speaking, cell subculturing includes the steps of: cleaning cells in a culture vessel; detaching the cells from the culture vessel; collecting cell suspension from the culture vessel; and seeding the cells collected from the cell suspension in a new culture vessel. In the cell subculturing, the step of detaching the cells from the culture vessel is one of the important steps since the detachment of the cells is a major factor that affects the amount of cells to be collected, the degree of damage to the cells, an engraftment rate thereafter, etc. The step of detaching the cells from the culture vessel includes the work of: treating the cells by means of, for example, a proteolytic enzyme such that the cells become easily detachable from the culture vessel; then pipetting by an operator; hitting the side and the bottom part of the culture vessel several times by the operator; and intensely shaking the culture vessel by the operator. The work of hitting the side and the bottom part of the culture vessel is called tapping.

Although the tapping was conventionally performed manually, there has been a proposal to mechanically automate the tapping. For example, Patent Literature 1 discloses a device for detaching cells from a culture vessel by repeatedly applying horizontal impact force to the culture vessel. This device includes: a placing stand, on which a flat culture vessel can be placed; and a vibration exciter configured to apply a pulse-like impact shock to the culture vessel. The vibration exciter includes a plunger configured to advance or retract by means of a solenoid. A hitting part configured to come into contact with the side of the culture vessel is provided on the distal end of the plunger.

CITATION LIST

Patent Literature

PTL 1: Japanese Laid-Open Patent Application Publication No. S58-158182

SUMMARY OF INVENTION

Technical Problem

When performing the tapping manually, an operator holds and supports a culture vessel with one hand, and taps the side of the culture vessel with the other hand several times. Through the tapping, both impact shocks and vibrations are applied to the culture vessel. According to an experiment conducted by the inventors of the present invention, merely applying either impact shocks or vibrations to a culture vessel was not enough to sufficiently detach cultured cells from the culture vessel. From this experiment, the inventors have found out that it is effective to apply both impact shocks and vibrations to the culture vessel for realizing sufficient and efficient detachment of the cultured cells.

In the device disclosed in Patent Literature 1, a recess slightly larger than the bottom part of the culture vessel is formed in the top surface of the placing stand, and the bottom part of the culture vessel is fitted in the recess with a slight play. Accordingly, the culture vessel hit by the vibration exciter is allowed to make slight horizontal movement in the recess of the placing stand. However, since the device of Patent Literature 1 is not a mechanism that actively causes the culture vessel to move, the culture vessel comes closer to the side wall of the recess each time the culture vessel is hit. Eventually, the culture vessel becomes unable to vibrate. In the device disclosed in Patent Literature 1, since the width of the vibration of the culture vessel is small, ripping of a liquid surface in the culture vessel is presumed to be insufficient for effectively facilitating the cell detachment.

The present invention has been made in view of the above. An object of the present invention is to sufficiently and efficiently detach cultured cells from a culture vessel by both vibrating the culture vessel while actively moving the culture vessel and applying impact shocks to the culture vessel, and to consequently achieve automated tapping.

Solution to Problem

A cell detachment device according to the present invention is a cell detachment device for detaching cultured cells from a culture vessel. The cell detachment device includes: a vessel holder, to which the culture vessel is to be fitted; a guide mechanism configured to guide reciprocating movement of the vessel holder; a collided member positioned at one end of a reciprocating movement range of the vessel holder; and an urging member configured to urge the vessel holder toward the collided member.

According to the above configuration, the vessel holder can move in a reciprocating manner while being guided by the guide mechanism. When the vessel holder moves, the culture vessel fitted to the vessel holder also moves. By thus causing the culture vessel to move in a reciprocating manner, the culture vessel can be vibrated. When the vessel holder moves with great force toward the collided member, the vessel holder or the culture vessel fitted thereto collides with the collided member with a great impact. In this manner, an impact shock can be applied to the vessel holder and the culture vessel. The impact shock applied to the culture vessel causes displacement between the culture surface of the culture vessel and the cells. In addition, a liquid surface in the culture vessel ripples owing to the vibration of the culture vessel, the impact shock received by the culture vessel, and a vibration caused by the impact shock. As a result, the cell detachment is facilitated. In this manner, the culture vessel vibrates and receives an impact shock. This makes it possible to sufficiently and efficiently detach the cells from the culture vessel.

Preferably, in the above cell detachment device, the collided member is configured to collide with the vessel holder.

According to the above configuration, the vessel holder collides with the collided member, but the culture vessel does not directly collide with the collided member. This makes it possible to prevent deformation of and damage to the culture vessel due to the impact shock. Moreover, since the vibration of the culture vessel and the impact shock received by the culture vessel can be made uniform over the entire culture vessel, unevenness in cell detachment is reduced, and an improvement in cell collection rate can be expected. Furthermore, even if the culture vessel has an increased size of the culture surface, the entire culture vessel evenly vibrates and evenly receives the impact shock. Therefore, unevenness in cell detachment is reduced, and an improvement in cell collection rate can be expected.

Preferably, the above cell detachment device includes a power imparting mechanism configured to impart, to the vessel holder, power for causing the vessel holder to move.

According to the above configuration, reciprocating movement of the vessel holder can be automated, and tapping can be automated. Accordingly, the vessel holder moves in a reciprocating manner periodically. This makes it possible to regularly apply a vibration and an impact shock to the culture vessel.

Preferably, in the above cell detachment device, the power imparting mechanism is configured to impart, to the vessel holder, force for causing the vessel holder to move in a direction away from the collided member.

According to the above configuration, the force imparted to the vessel holder by the power imparting mechanism causes the vessel holder to move in a direction away from the collided member. When the force is eliminated, the urging force of the urging member causes the vessel holder to move with great force in a direction toward the collided member. In this manner, the vessel holder can be caused to move in a reciprocating manner. Also, the vessel holder or the culture vessel can be caused to collide with the collided member with a great impact.

Preferably, in the above cell detachment device, the power imparting mechanism includes: a motor; and a cam configured to convert a rotation output of the motor into force acting on the vessel holder. More preferably, the cam includes: an action part acting on the vessel holder when a rotation angle of the cam is in a predetermined action range; and an action-receiving part not acting on the vessel holder when the rotation angle of the cam is out of the predetermined action range.

According to the above configuration, the vessel holder is caused to move in a reciprocating manner periodically. This makes it possible to regularly apply a vibration and an impact shock to the vessel holder.

Preferably, in the above cell detachment device, the power imparting mechanism includes a controller, and the controller controls operation of the power imparting mechanism such that the number of collisions between the vessel holder or the culture vessel fitted to the vessel holder and the collided member becomes a predetermined number of impact shocks.

Preferably, the above cell detachment device includes: a rotation number sensor configured to detect the number of rotations of the cam; and a controller configured to control operation of the motor in accordance with a detection output that the controller receives from the rotation number sensor. The controller controls the operation of the motor such that the number of rotations of the cam becomes a predetermined number of impact shocks.

According to the above configuration, an optimal number of impact shocks to apply for causing the cells to be detached from the culture vessel can be imparted to the culture vessel. This makes it possible to prevent insufficient cell detachment, and prevent excessive vibrations or impact shocks from being imparted to the culture vessel after the cells are detached from the culture vessel.

Preferably, in the above cell detachment device, the urging member is a spring.

The above configuration allows the vessel holder to continue vibrating after colliding with the collided member. This makes it possible to apply a vibration to the culture vessel held by the vessel holder.

Preferably, the above cell detachment device includes a second collided member, which is disposed at another end of the reciprocating movement range of the vessel holder.

According to the above configuration, the vessel holder comes into contact with the collided members in both forward and backward paths of the reciprocating movement. In this manner, the vessel holder can receive impact shocks.

Advantageous Effects of Invention

According to the present invention, both an impact shock and a vibration can be applied to the culture vessel. The detachment of the cultured cells from the culture vessel is facilitated by rippling of the liquid surface, which is caused by the impact shock and the vibration applied to the culture vessel. As a result, the cultured cells can be sufficiently and efficiently detached from the culture vessel.

BRIEF DESCRIPTION OF DRAWINGS

FIG. 1 is a plan view showing an overall schematic configuration of a cell detachment device according to one embodiment of the present invention.

FIG. 2 is a schematic plan view of the cell detachment device, showing a state where a vessel holder has moved from a reference position.

FIG. 3 is a plan view showing a schematic configuration of a cell detachment device according to Variation 1.

FIG. 4 is a plan view showing a schematic configuration of a cell detachment device according to Variation 2.

DESCRIPTION OF EMBODIMENTS

Hereinafter, one embodiment of the present invention is described with reference to the drawings. FIG. 1 is a plan view showing an overall schematic configuration of a cell detachment device 1 according to one embodiment of the present invention. FIG. 2 is a schematic plan view of the cell detachment device 1, showing a state where a vessel holder 11 has moved from a reference position P. In FIG. 1 and FIG. 2, a flask-shaped culture vessel 2 is indicated by a two-dot chain line. Cells cultured in the culture vessel 2 adhere to the culture surface (mainly the inner bottom surface) in the culture vessel 2. The cell detachment device 1 is a device for detaching the cells from the culture surface of the culture vessel 2.

As shown in FIG. 1, the cell detachment device 1 includes: a base 10; the vessel holder 11, to which the culture vessel 2 is fitted; a guide mechanism 21 configured to guide reciprocating movement of the vessel holder 11; a collided member 33 configured to collide with the vessel holder 11 when the vessel holder 11 is moving; and an urging member 31 configured to urge the culture vessel 2 toward the collided member 33. The cell detachment device 1 further includes a power imparting mechanism 41 configured to impart, to the vessel holder 11, power for causing the vessel holder 11 to move while being guided by the guide mechanism 21. The vessel holder 11, the guide mechanism 21, the collided member 33, the urging member 31, and the power imparting mechanism 41 are each provided on the base 10. Hereinafter, the components of the cell detachment device 1 are described in detail.

(Vessel Holder 11)

The vessel holder 11 includes a plate-shaped board 12 and a holding frame 13 fixed on the board 12. One or a plurality of protrusions provided in a manner to rim at least four edges of the outline of the culture vessel 2 serve as the holding frame 13. When the culture vessel 2 is placed in the holding frame 13, movement of the culture vessel 2 substantially in the horizontal direction is restricted by the holding frame 13. The vessel holder 11 configured as above holds the culture vessel 2, such that the culture vessel 2 is unable to move substantially in the horizontal direction relative to the vessel holder 11, and the vessel holder 11 moves integrally with the culture vessel 2 substantially in the horizontal direction.

Desirably, the vessel holder 11 can hold the culture vessel 2 even if the size and type of the culture vessel 2 vary among a plurality of sizes and types. Therefore, for example, a plurality of types of vessel holders 11 may be fabricated, and the vessel holder 11 to use may be changed in accordance with the shape of the culture vessel 2. Alternatively, for example, a plurality of components attachable to and detachable from the board 12 may serve as the holding frame 13, and the attachment position of each component of the holding frame 13 on the board 12 may be changed in accordance with the shape of the culture vessel 2.

(Guide Mechanism 21)

The guide mechanism 21 includes one or a plurality of linear motion guides. The guide mechanism 21 according to the present embodiment includes two sets of linear motion guides. The two sets of linear motion guides include two rails 22 and four sliders 23. Two sliders 23 slidingly move on each rail 22. The two rails 22 are arranged substantially parallel to each other on the base 10, and are fixed to the base 10. The four sliders 23 are arranged and fixed on the lower surface of the board 12 in such a manner that the sliders 23 can support the vessel holder 11 in a balanced manner. The guide mechanism 21 with the above-described configuration guides the vessel holder 11 in a manner to allow the vessel holder 11 to make smooth reciprocating movement in a substantially horizontal direction relative to the base 10, and supports the vessel holder 11. Hereinafter, the direction in which the vessel holder 11 moves in a reciprocating manner is simply referred to as a "moving direction X".

(Collided Member 33)

The collided member 33 is a member configured to come into contact with the vessel holder 11 at the reference position P. The collided member 33 is a member configured to collide with the vessel holder 11 when the vessel holder 11 has made reciprocating movement and reached the reference position P. The state where the vessel holder 11 is at the "reference position P" is a state where the vessel holder 11 is positioned at one end of a reciprocating movement range of the vessel holder 11, the one end being a starting point of the reciprocating movement of the vessel holder 11. The collided member 33 is provided at the one end of the reciprocating movement range of the vessel holder 11. To be more specific, the collided member 33 is disposed such that the collided member 33 is lateral to the vessel holder 11 when the vessel holder 11 is at the reference position P, and is disposed on one side of the moving direction X outside the reciprocating movement range. Although the collided member 33 shown in FIG. 1 is in the shape of a block that is long in a direction substantially perpendicular to the moving direction X, the shape of the collided member 33 is not limited to a block shape, but the collided member 33 may be plate-shaped or columnar, for example.

(Urging Member 31)

The urging member 31 is a member for urging the vessel holder 11 toward the collided member 33. The urging member 31 according to the present embodiment is a tension spring disposed such that the tension spring expands and contracts substantially parallel to the moving direction X. One end of the urging member 31 is fixed to the board 12 of the vessel holder 11, and the other end of the urging member 31 is fixed to the base 10. When the vessel holder 11 is at the reference position P, the tension spring serving as the urging member 31 is in the state of expanding from its natural length and is elastically deformed. While the power imparting mechanism 41 is not in operation, the vessel holder 11 is in a standby state. In the standby state, the vessel holder 11 is at the reference position P and is in contact with the collided member 33 due to the action of the urging member 31.

(Power Imparting Mechanism 41)

The power imparting mechanism 41 includes a motor 43 as a device that generates power for causing the vessel holder 11 to move. A power transmission system for transmitting the power from the motor 43 to a cam 45 is constructed so that rotational power can be transmitted from the output shaft of the motor 43 to the cam 45 directly or indirectly. The power imparting mechanism 41 further includes: a controller 42 configured to control the operation of the motor 43; a contacting or non-contacting rotation number sensor 46 configured to detect and output the number of rotations of the cam 45 to the controller 42; and an input device 47, with which an input to the controller 42 is made. For example, a counting limit switch may be used as the rotation number sensor 46. The input device 47 includes; an operation switch for switching the device operation state between an operating state and an operation stopped state; and an input unit, with which to input the number of impact shocks to apply to the vessel holder 11.

The cam 45 serves to convert a rotation output of the motor 43 into force for causing the vessel holder 11 to move, the force acting on the vessel holder 11. The cam 45 outputs rotational power of the motor 43 as force pushing the vessel holder 11 in the moving direction X away from the collided member 33. An action part 45*a* acting on the vessel holder 11 is formed on the cam 45. When the rotation angle of the cam 45 is in a predetermined action range, the action part 45*a* of the cam 45 pushes an action-receiving part 15 of the vessel holder 11. In this manner, force causing the vessel holder 11 to move in the moving direction X away from the collided member 33 is imparted to the vessel holder 11. On the other hand, when the rotation angle of the cam 45 is out of the action range (i.e., in a non-action range), the action part 45*a* of the cam 45 does not act on the vessel holder 11. Accordingly, if the cam 45 rotates several revolutions, pushing force will be imparted to the vessel holder 11 intermittently. Although the action range of the cam 45 shown in FIG. 1 is 90° to 180°, the action range of the cam 45 may be suitably set.

Hereinafter, the operation of the cell detachment device 1 is described. In preparation for operating the cell detachment device 1, the culture vessel 2 is fitted to the vessel holder 11 at the reference position P. At the time, cells in the culture vessel 2 have already been treated by means of a proteolytic enzyme or the like so that the cells can be readily detached from the culture vessel 2.

An operator turns on the operation switch after setting the number of impact shocks to apply by the input device 47. In response, the controller 42 causes the motor 43 to operate such that the cam 45 rotates a number of revolutions corresponding to an optimal number of impact shocks to apply, which is inputted from the input device 47.

When the motor 43 is driven, the cam 45 rotates, accordingly. When the rotation angle of the cam 45 falls within the action range, the cam 45 pushes the vessel holder 11 in a direction away from the collided member 33. In other words, force causing the vessel holder 11 to move in the direction away from the collided member 33 is imparted to the vessel holder 11. As a result, the vessel holder 11 moves in the direction away from the collided member 33 against the urging force of the urging member 31 (see FIG. 2). It should be noted that, in the present embodiment, a moving stroke of the vessel holder 11 when the vessel holder 11 is pushed by the cam 45 is approximately 10 mm. Desirably, the moving stroke of the vessel holder 11 in its reciprocating movement is 10 mm or more.

When the rotation angle of the cam 45 has shifted from the action range into the non-action range, the pushing force imparted to the vessel holder 11 by the cam 45 is eliminated. Accordingly, the urging force of the urging member 31 causes the vessel holder 11 to move in the moving direction X toward the collided member 33. As a result of moving in the moving direction X toward the collided member 33, the vessel holder 11 collides with the collided member 33. At the time, the collided member 33 applies an impact shock to the vessel holder 11, and also restricts the movement of the vessel holder 11 in a direction toward the collided member 33. After colliding with the collided member 33, the vessel holder 11 temporarily moves away from the collided member 33 by counteraction. Thereafter, the vessel holder 11 moves toward the collided member 33 again owing to the urging force of the urging member 31. In this manner, after colliding with the collided member 33, the vessel holder 11 continues vibrating with a reduced vibration width. The spring constant of the urging member 31 is suitably chosen so that the vibration having such a reduced vibration width will occur. The vibration diminishes, and the vessel holder 11 eventually stops at the reference position P.

When the rotation angle of the cam 45 has shifted from the non-action range into the action range again, the vessel holder 11 repeats the above-described reciprocating movement and collision with the collided member 33. The series of operations of the cell detachment device 1 thus described is repeated for a number of times corresponding to the set number of impact shocks to apply. An impact shock and a vibration are regularly applied to the vessel holder 11 by a number of times corresponding to the number of impact shocks to apply. An optimal number of impact shocks to apply is different depending on the type and culturing conditions of the cells. Therefore, it is desirable to experimentally obtain the minimum number of impact shocks to apply necessary for detaching the cells from the culture vessel 2, and set it as the number of impact shocks to apply.

When the vessel holder 11 moves in a reciprocating manner while being guided by the guide mechanism 21 in the above-described manner, the culture vessel 2 fitted to the vessel holder 11 also moves. By thus causing the culture vessel 2 to move in a reciprocating manner, the culture vessel 2 can be vibrated. When the vessel holder 11 collides with the collided member 33 as described above, an impact shock received by the vessel holder 11 is transmitted to the culture vessel 2. In addition, a vibration is applied to the culture vessel owing to the impact shock received by the vessel holder 11. In this manner, the cell detachment device 1 can perform both vibrating the culture vessel 2 and applying an impact shock to the culture vessel 2. The impact shock applied to the culture vessel 2 causes displacement between the culture surface of the culture vessel 2 and the cells. In addition, a liquid surface in the culture vessel 2 ripples owing to the vibration of the culture vessel 2, the impact shock received by the culture vessel 2, and a vibration caused by the impact shock. As a result of the rippling of the liquid surface, the cell detachment is facilitated. Thus, according to the cell detachment device 1 of the present embodiment, the culture vessel 2 vibrates and receives an impact shock. This makes it possible to sufficiently and efficiently detach the cells from the culture vessel 2.

In the above-described operation of the cell detachment device 1, the collided member 33 makes a direct collision not with the culture vessel 2 but with the vessel holder 11, This makes it possible to move (vibrate) the entire outer bottom surface of the culture vessel 2 in a single direction in a single amount and make the manner in which the impact shock is transmitted to the culture vessel 2 uniform. Moreover, even if the culture vessel 2 has an increased size of the culture surface, the impact shock and vibration can be evenly transmitted in the culture vessel 2. Since the vibration and impact shock are evenly transmitted to the culture vessel 2 in this manner, unevenness in the cell detachment can be reduced. This consequently makes it possible to improve the cell collection rate. Furthermore, since the collided member 33 does not make a direct collision with the culture vessel 2, deformation of and damage to the culture vessel 2 can be prevented. It should be noted that, in conventional manual tapping, since the culture vessel is directly hit, the impact shock tends to be transmitted unevenly. In addition, in a case where the culture vessel has a large culture surface area, it is necessary to hit several parts of the culture vessel. This further increases unevenness in the transmission of the impact shock. The cell detachment device 1 according to the present embodiment also solves these problems.

Although one preferred embodiment of the present invention has been described above, the configuration described above may be modified, for example, in a manner described below.

As one example, although the above-described cell detachment device 1 includes the motor 43 and the cam 45 as the power imparting mechanism 41, the cell detachment device 1 may be modified such that the motor 43 and the cam 45 are replaced by solenoid actuators with moving cores. Thus, the configuration of the power imparting mechanism 41 is not limited to the one described in the above embodiment, and the power imparting mechanism 41 may be configured in any manner, so long as the power imparting mechanism 41 is configured to impart the force for causing the reciprocating movement of the vessel holder 11 to the vessel holder 11 or the guide mechanism 21.

As another example, although the vessel holder 11 directly collides with the collided member 33 in the above-described cell detachment device 1, the cell detachment device 1 may be modified such that the collided member 33 makes a direction collision with the culture vessel 2. In this case, it is desirable to set the contact surface of the collided member 33 sufficiently large so that the culture vessel 2 will receive the impact shock more evenly. In addition, it is desirable that cushioning be provided on the contact surface of the collided member 33.

As yet another example, although the collided member 33 is disposed at one end of the reciprocating movement range of the vessel holder 11 in the above-described cell detachment device 1, the collided member 33 may be disposed at both sides of the reciprocating movement range. FIG. 3 is a plan view showing a schematic configuration of a cell detachment device according to Variation 1. In FIG. 3 and the description below, components that are the same as or similar to those described in the above embodiment are denoted by the same reference signs as those used in the above embodiment, and repeating the same descriptions is avoided. In the cell detachment device 1 shown in FIG. 3, a first collided member 33A is disposed outside of one end of the reciprocating movement range of the vessel holder 11, and a second collided member 33B is disposed outside of the other end of the reciprocating movement range of the vessel holder 11. According to this configuration, the vessel holder 11 collides with the first collided member 33A after moving forward from the reference position P, and then collides with the second collided member 33B after moving forward. That is, the vessel holder 11 collides with the collided members 33A and 33B in the forward and backward paths of the reciprocating movement, respectively, thereby receiving impact shocks. In this manner, the number of impact shocks to apply can be increased relative to the number of vibrations of the vessel holder 11, and thereby the cell detachment from the culture vessel 2 can be facilitated.

As yet another example, in the above-described cell detachment device 1, the tension spring serving as the urging member 31 may be replaced by a compression spring. FIG. 4 is a plan view showing a schematic configuration of a cell detachment device according to Variation 2. In FIG. 4 and the description below, components that are the same as or similar to those described in the above embodiment are denoted by the same reference signs as those used in the above embodiment, and repeating the same descriptions is avoided. As shown in FIG. 4, an urging member 31A, which is a compression spring, is disposed at the opposite side to the collided member 33 with the vessel holder 11 positioned between the urging member 31A and the collided member 33, such that the urging member 31A expands and contracts substantially parallel to the moving direction X. One end of the urging member 31A is fixed to the base 10, and the other end of the urging member 31A is fixed to the vessel holder 11. According to this configuration, when the vessel holder 11 receives pushing force from the cam 45 and moves in a direction away from the collided member 33, the urging member 31A is compressed. When the pushing force applied to the vessel holder 11 from the cam 45 is eliminated, the urging member 31A recovers elastically, and thereby the vessel holder 11 is urged toward the collided member 33. Although a spring is adopted as the urging member 31 in the above-described cell detachment device 1, the urging member 31 is not limited to a spring, but may be an elastic member such as rubber.

While the embodiment and the variations of the present invention have been described above with reference to the drawings, it will be understood that those skilled in the art, upon attaining an understanding of the foregoing, will readily conceive of various alterations and modifications without departing from the scope of the present invention. Therefore, such alterations and modifications are construed to fall within the scope of the present invention, which is defined by the claims.

REFERENCE SIGNS LIST

1 cell detachment device
2 culture vessel
11 vessel holder
12 board
13 holding frame
15 action-receiving part
21 guide mechanism
22 rail
23 slider
31 urging member
33 collided member
41 power imparting mechanism
42 controller
43 motor
45 cam
45a action part
46 rotation number sensor
47 input device

The invention claimed is:

1. A cell detachment device comprising:
a culture vessel with cultured cells attached;
a vessel holder, to which the culture vessel is to be fitted, the vessel holder including a board and a holding frame fixed on the board, the holding frame being formed by one or a plurality of protrusions that rim an outline of the culture vessel place on the board;
a guide mechanism configured to guide reciprocating movement of the vessel holder;
a collided member positioned at one end of a reciprocating movement range of the vessel holder;
a power imparting mechanism configured to impart, to the vessel holder, power for causing the vessel holder to move; and
an urging member configured to urge the vessel holder toward the collided member, wherein:
the vessel holder is reciprocated, while being guided by the guide mechanism, by an urging force of the urging member, such that only a side surface of the board of the vessel holder collides with the collided member at an end of the reciprocating movement range so that the cultured cells are detached from the culture vessel,
the power imparting mechanism includes a controller, and
the controller controls operation of the power imparting mechanism such that the number of collisions between the vessel holder or the culture vessel fitted to the vessel holder and the collided member becomes a predetermined number of impact shocks.

2. The cell detachment device according to claim 1, wherein
the power imparting mechanism is configured to impart, to the vessel holder, force for causing the vessel holder to move in a direction away from the collided member.

3. The cell detachment device according to claim 1, wherein
the power imparting mechanism includes:
a motor; and
a cam configured to convert a rotation output of the motor into force acting on the vessel holder.

4. The cell detachment device according to claim 3, wherein
the cam acts on the vessel holder when a rotation angle of the cam is in a predetermined action range, and the cam does not act on the vessel holder when the rotation angle of the cam is out of the predetermined action range.

5. The cell detachment device according to claim 1, wherein the urging member is a spring.

6. The cell detachment device according to claim 1, comprising a second collided member, which is disposed at another end of the reciprocating movement range of the vessel holder.

7. A cell detachment device comprising:
a culture vessel with cultured cells attached;
a vessel holder, to which the culture vessel is to be fitted, the vessel holder including a board and a holding frame fixed on the board, the holding frame being formed by one or a plurality of protrusions that rim an outline of the culture vessel place on the board;
a guide mechanism configured to guide reciprocating movement of the vessel holder;

a collided member positioned at one end of a reciprocating movement range of the vessel holder;
a power imparting mechanism configured to impart, to the vessel holder, power for causing the vessel holder to move; and
an urging member configured to urge the vessel holder toward the collided member, wherein:
the vessel holder is reciprocated, while being guided by the guide mechanism, by an urging force of the urging member, such that only a side surface of the board of the vessel holder collides with the collided member at an end of the reciprocating movement range so that the cultured cells are detached from the culture vessel,
the power imparting mechanism includes:
  a motor; and
  a cam configured to convert a rotation output of the motor into force acting on the vessel holder,
the cell detachment device further includes:
  a rotation number sensor configured to detect the number of rotations of the cam; and
  a controller configured to control operation of the motor in accordance with a detection output that the controller receives from the rotation number sensor, and the controller controls the operation of the motor such that the number of rotations of the cam becomes a predetermined number of impact shocks.

8. The cell detachment device according to claim 7, wherein
the power imparting mechanism is configured to impart, to the vessel holder, force for causing the vessel holder to move in a direction away from the collided member.

9. The cell detachment device according to claim 7, wherein
the cam acts on the vessel holder when a rotation angle of the cam is in a predetermined action range, and the cam does not act on the vessel holder when the rotation angle of the cam is out of the predetermined action range.

10. The cell detachment device according to claim 7, wherein the urging member is a spring.

11. The cell detachment device according to claim 7, comprising a second collided member, which is disposed at another end of the reciprocating movement range of the vessel holder.

* * * * *